United States Patent [19]
Langner et al.

[11] Patent Number: 5,817,855
[45] Date of Patent: Oct. 6, 1998

[54] COPPER-BASED CATALYSTS, PROCESSES FOR THEIR PRODUCTION AND THEIR USE AND A PROCESS FOR THE PRODUCTION OF ALKYL HALOSILANES

[75] Inventors: Bernd Langner, Winsen/Luhe; Peter Stantke, Buxtehude; Thomas Leister, Lübeck; Matthias-Sven Steiner, Leverkusen; Bruno Degen, Much; Wolfgang Schartau; Elke Licht, both of Leverkusen, all of Germany

[73] Assignees: Bayer Aktiengesellschaft, Leverkusen; Norddeutsche Affinerie Aktiengesellschaft, Hamburg, both of Germany

[21] Appl. No.: 755,499

[22] Filed: Nov. 22, 1996

[30] Foreign Application Priority Data

Dec. 1, 1995 [DE] Germany .................. 195 44 748.4
May 11, 1996 [DE] Germany .................. 196 19 161.0

[51] Int. Cl.$^6$ ........................................ C07F 7/16
[52] U.S. Cl. .................... 556/472; 502/343; 502/345
[58] Field of Search ................ 556/472; 502/343; 1/345

[56] References Cited

U.S. PATENT DOCUMENTS 2,380,995 8/1945 Rochow .
2,420,540 5/1947 Hubbell .
4,218,387 8/1980 Maas et al. .
4,487,950 12/1984 Ward, III et al. .
4,504,597 3/1985 Klar et al. .
4,520,130 5/1985 Hashiguchi et al. .
4,762,940 8/1988 Halm et al. .

FOREIGN PATENT DOCUMENTS 0620226 10/1994 European Pat. Off. .
2153697 8/1985 United Kingdom .

OTHER PUBLICATIONS

P.J. Heinzer, Particle Shape Analysis, pp. 233–245.

E. Klar, Production of Metal Powders, Metals Handbook® Ninth Edition American Society for Metals, vol. 7, pp. 105–110.

E. Klar, Production of Metal Powders, pp. 116–122.

Primary Examiner—Paul F. Shaver
Attorney, Agent, or Firm—Sprung Kramer Schaefer & Briscoe

[57] ABSTRACT

The invention relates to copper-based catalysts, processes for their production and their use and to a process for the production of alkyl halosilanes in the presence of said catalysts.

16 Claims, 1 Drawing Sheet

<40 μm    21696    10 μm 050    21700    3 μm

COPPER-BASED CATALYSTS, PROCESSES FOR THEIR PRODUCTION AND THEIR USE AND A PROCESS FOR THE PRODUCTION OF ALKYL HALOSILANES

BACKGROUND OF THE INVENTION

This invention relates to copper-based catalysts, processes for their production and their use and to a process for the production of alkyl halosilanes in the presence of said catalysts. A large number of copper catalysts have been proposed in the past 50 years for the reaction of ground silicon with alkyl halide to form alkyl halosilanes (the Rochow synthesis, e.g. U.S. Pat. No. 2 380 995). Thus between 1940 and about 1980 not only were mixtures of metallic copper and $Cu_2O/CuO$ (DE-A 3 501 085), $Cu_2Cl_2$, $CuCl_2$(U.S. Pat. No. 4,762,940) and copper formate (U.S. PAt. No. 4,487,950) used but also, inter alia, very fine hydrometallurgical cements which were precipitated from copper solutions by the addition of iron and were in some cases subsequently oxidized (see for example U.S. Pat. No. 2,420,540). Since the cements were usually produced from solutions of oxidic copper ores and the cementation and possible subsequent oxidation could only be controlled with difficulty, problems repeatedly occurred on attempting to guarantee the reproducible catalytic activity of these cements for the synthesis of silanes.

For the above reason and due to the fact that this type of oxidized copper was almost no longer available in the 70's, the search began for other sources of oxidized copper catalysts. In general both electrolytic copper, atomized copper powders and chemically precipitated copper powders can be used as the starting material for the oxidation, or coarser copper fragments are used. In order to increase activity, metals or metal compounds are additionally added to the copper catalyst or its precursors in concentrations of 0.1 to 10%. In addition to zinc or zinc compounds and aluminium or aluminium compounds, tin is considered to be an important additive. As a result the catalysts usually contain between 400 and 3,000 ppm of tin. In addition to the promoters, catalyst poisons such as lead, do however also exist, whose concentration should therefore be below 100 ppm.

In all cases the original copper material or the alloy is oxidized by pyrometallurgical oxidation (U.S. Pat. No. 4,520,130 and U.S. Pat. No. 4,504,597) in air or at low oxygen partial pressures (U.S. Pat. No. 4,218,387) to form a mixture of copper and its oxides. It is important for the activity of the catalyst to include specific contents of copper (approx. 2 to 30%), copper(I) oxide (approx. 30 to 70%) and copper(II) oxide (approx. 10 to 30%). When oxidizing copper catalysts not produced by cementation it is however necessary for the obtainment of high catalytic activity to use high-energy grinding in order to produce a powder with high BET surface areas of higher than 1 $m^2/g$ and very small particle sizes of approximately 2 to 7 $\mu m$. As is known, crystal lattice distortions promote catalytic activity (see U.S. Pat. No. 4,520,130 and U.S. Pat. No. 4,504,597).

Not only does the high amount of energy required for high-energy grinding result in high production costs but high indirect costs are also incurred, since the machines used undergo a high degree of abrasion. The processes described are also disadvantageous from a chemical point of view, since, when the catalyst is used in a fluidized bed reactor its low particle sizes mean that the catalyst particles are discharged relatively quickly from the reactor and are thus no longer available for the catalytic process. Thus one is either forced to accept poor catalytic results or correspondingly high quantities of catalyst have to be provided, as a result of which the costs are also increased. In addition, the abrasion which occurs during high-energy grinding leads to contamination of the substance.

SUMMARY OF THE INVENTION

The present invention is directed towards providing copper-based catalysts which have a small BET surface area, can be obtained without any reduction in particle size as a result of high-energy grinding and can be produced simply with any desired contents of doping elements. In addition the catalysts according to the invention must be capable of being used in the Rochow process for the production of alkyl halosilanes. The promoters possibly necessary for this purpose should preferably be contained in the copper-containing catalysts, in order to avoid the complicated metering and mixing of components before their introduction into the Rochow reactor.

DETAILED DESCRIPTION

It has now been found that the copper-based catalysts according to the invention, which have a BET surface area of between 0.05 and less than 0.5 $m^2/g$ and an average particle diameter of between 1 and 200 $\mu m$, solve the above problems. The invention therefore relates to copper-based catalysts which have the following composition:

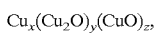

provided that x +y +z =1,
preferably
    x=0 to 0.3, more preferably 0.005 to 0.2
    y=0.2 to 0.9, more preferably 0.4 to 0.8
    z=0.1 to 0.6, more preferably 0.3 to 0.5,
also with the provision that x+y+z=1,
a BET surface area of between 0.05 and less than 0.5 $m^2/g$ and an average particle diameter of between 1 and 200 $\mu m$.

The BET surface area was determined with the aid of a Flow-Sorb 2/2300 device from Micrometrics using $N_2$ as an agent to be adsorbed.

In a preferred embodiment of the invention x=0 to 0.3 and x+y+z=1 in the catalysts according to the invention and they have a spongy surface at least before the oxidation of the metallic copper used as the starting substance.

The characteristic appearance of the type of surface structure referred to in the present context as spongy is described in the handbook "Metals Handbook, 9th Edition, Volume 7, Powder Metallurgy, American Society for Metals, in the sections Copper Powder/107, Copper Powder/117, and in the chapter Particle Shape Analysis".

BRIEF DESCRIPTION OF THE DRAWINGS

FIG. 1 shows such a spongy surface of the catalyst according to the invention. It can be seen that the three-dimensional structures have diameters in the range from 1 to 20 $\mu m$ and partly adhere to one another.

In an additional, equally preferred embodiment of the invention the values for x in the copper-based catalyst are less than 0.3.

If x is smaller than 1.0 in the catalyst according to the invention (after oxidation) the surface structure is different from that of the completely or almost completely non-oxidized catalyst.

Figure 1:
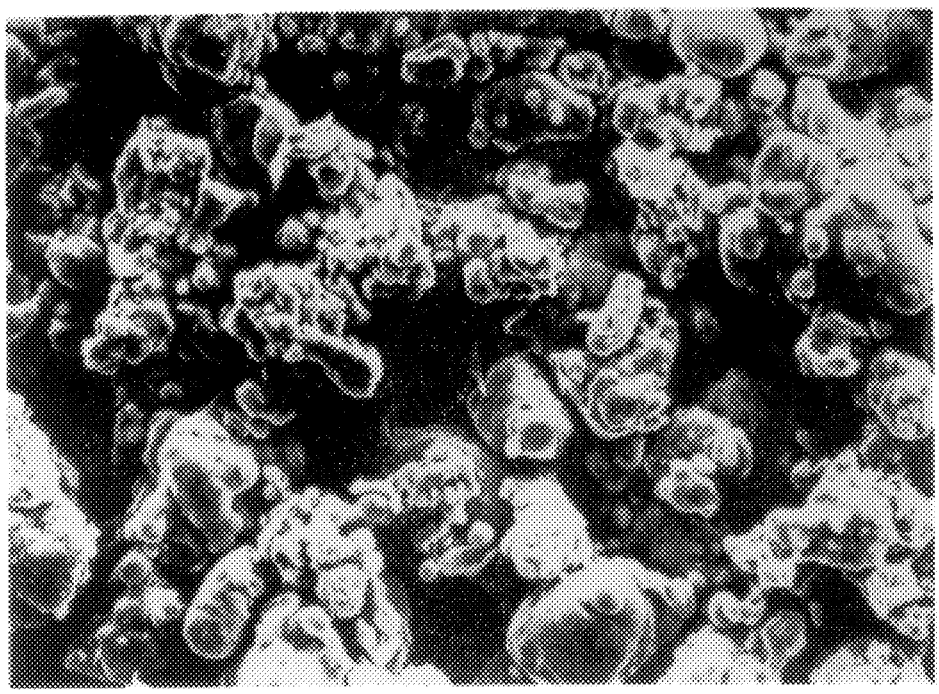
FIG. 1 is an electron micrograph of the catalyst of the present invention.
Figure 2:
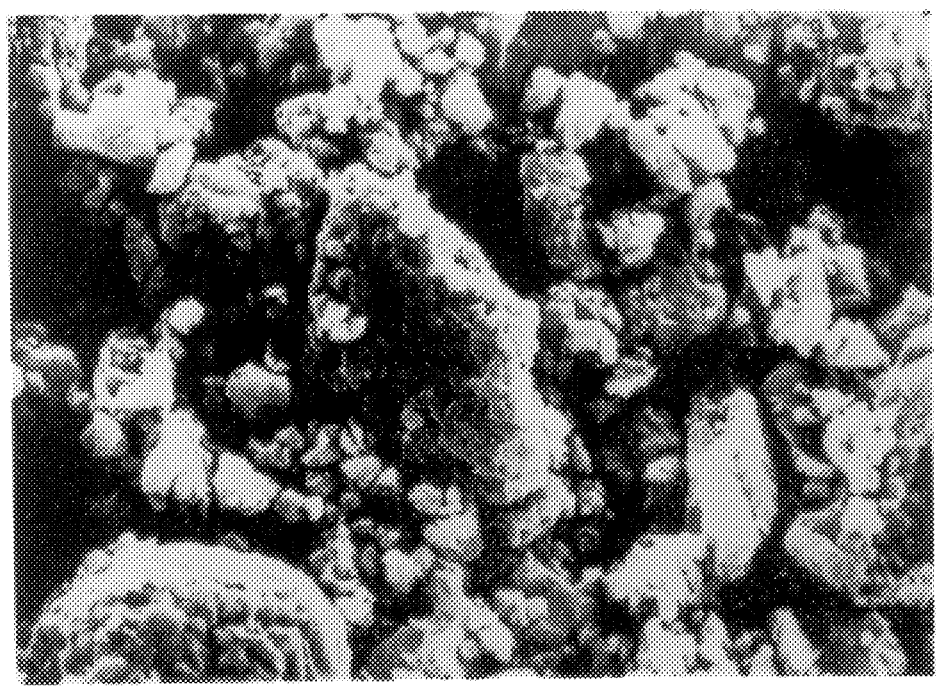
FIG. 2 is an electron micrograph of the catalyst of the present invention after carrying out the oxidation process.

FIG. 2 shows the surface structure after carrying out the oxidation process. It is noticeable that after the oxidation process has been carried out a complex surface structure is present in which a large number of variously sized surfaces have merged into each other in a crystal-like manner. Thus, in contrast to high-energy grinding, a uniform shape is obtained over a very large surface region, in which metallic copper, copper(I) oxide and copper(II) oxide are arranged one on top of each other in the form of shells. The individual layer thicknesses and the strength of the adhesion between the superimposed layers are very similar over the major portion of the catalyst particle.

The provision of a special geometrical structure of the surface regions of the copper-based catalysts represents a very important part of the present invention.

In a preferred embodiment of the invention the catalysts according to the invention contain doping elements. In principle it is also possible to use smaller amounts of metallic copper, or, if metallic copper is not available, merely superimposed mutually adhering layers of $Cu_2O$ and CuO.

Preferably the catalysts are doped with at least one element from the group consisting of tin, zinc, aluminium, iron, antimony, arsenic, phosphorus and alkali metals and/or alkaline earth metals, either in elemental form or in the form of their compounds.

The copper-based catalysts therefore preferably contain up to 10,000 ppm of at least one added element. Preferably the catalysts contain up to 3,000 ppm, and more preferably between 10 and 800 ppm of tin, magnesium, iron, antimony, arsenic, calcium, phosphorus, aluminium and/or zinc.

The present invention also relates to a copper-based catalyst obtainable by atomizing molten metallic copper in a receiving medium having a temperature which is lower than the melting temperature of the copper, followed by the isolation of the solidified copper particles and their oxidation.

As a result of the atomization of the metallic copper the copper particles formed are shaped in such a manner that a highly active catalyst is obtained after carrying out the oxidation process. It is not necessary to comminute the catalyst to very small particle sizes accompanied by crystal lattice distortions by means of high-energy grinding, but as a rule the catalyst can already be used in the form resulting from the process. If necessary, it is possible to conduct screening or some other form of separation process in order to select those particles to be subsequently used. Also, where undesired agglomeration processes take place, it is possible to carry out subsequent comminution, and in particular deagglomeration, in order to ensure sufficiently thorough mixing with the substances to be catalysed and to increase the yield. In particular, the resulting relatively large particle size of the catalyst renders it excellently suitable for use in the field of fluidised bed reactors.

Both a liquid and a gaseous receiving medium are suitable for the atomization process.

In view of the oxidation which has to be carried out after atomization it has proven advantageous for the receiving medium to be water.

The liquid receiving medium can however also consist of oils, such as for example paraffin oils or silicone oils, either by themselves or in the form of mixtures or in combination with water.

The preferred gaseous receiving medium is air, water vapour, oxygen, nitrogen and/or an inert gas. Air or water vapour are particularly preferred.

The pressure during atomization and the size of the nozzles are appropriately set so that at least 50% of the copper particles formed during atomization have a particle size ($d_{50}$) of less than 100 micrometres.

Atomization in the liquid receiving medium is preferably carried out at an atomization pressure of 50 to 500 bars. A pressure of 50 to 300 bars is particularly preferred.

Atomization in a gaseous receiving medium is preferably carried out at an atomization pressure of 0.1 to 15 bars, preferably 6 to 12 bars.

The preferred metallic copper is electrolytic copper with a lead content of less than 100 ppm, preferably less than 40 ppm, and copper alloys are also preferred.

Preferred copper alloys are alloys containing at least one of the elements tin, zinc, aluminium, iron, antimony, arsenic, phosphorus and alkali metals and/or alkaline earth metals, either in elemental form or in the form of their compounds.

Compounds are for example alloys, metal phosphides or metal silicides.

In the event of doping with alkali metals and/or alkaline earth metals the quantity is preferably 1 to 10,000 ppm. The quantity of the remaining doping elements is 1 to 3,000 ppm, and preferably up to 800 ppm per element.

If atomization is carried out in a gaseous medium preferably 1 to 10 000 ppm of one or more elements from the group consisting of the alkali metals and/or alkaline earth metals are added. Immediately after atomization using gas, the emerging particles of molten metal have a very uneven shape which becomes almost spherical after a certain time if the copper catalyst is not in the form of an alloy. Due to the abovementioned additives an oxide layer is however formed on the molten metal shortly after the emergence of the particles from the nozzle which stabilizes the existing shape and prevents any transformation into a spherical shape, despite the fact that liquid metal is still contained for a long time inside the oxidic shell.

The melting of the copper or the copper alloy is preferably carried out in an induction furnace. After atomization in the liquid medium the resulting copper powder is preferably first dried and then subjected to the oxidation process. The oxidation can for example be carried out in an indirectly electrically heated rotary kiln, in a stirred reactor or in a fluidized bed. Appropriate temperature ranges are between 100° C. and 1,000° C., preferably between 300° C. and 900° C. and particularly advantageously between 400° C. and 800° C.

Suitable residence times for carrying out the oxidation are between 5 and 120 minutes. Residence times in the range from 10 to 90 minutes are particularly advantageous.

The boundary conditions of the oxidation process are preferably predetermined so that the oxidation process is carried out in such a manner that the catalyst contains 0 to 30%, preferably 0.5 to 20%, of metallic copper, 30 to 90%, preferably 40 to 80%, of copper(I) oxide and preferably 10 to 60%, and in particular 30 to 50% of copper(II) oxide. All the percentages are based on weight.

A typical oxidation process can be defined as being carried out with at least partial sintering.

The BET surface area of the catalyst according to the invention is preferably 0.05 to 1 $m^2/g$, and more preferably 0.05 to 0.5 $m^2/g$, as measured with a Flow-Sorb 2/2300 device from Micrometrics using $N_2$ as an agent to be adsorbed.

The activity of the catalyst can be additionally increased by adding to the oxidation process only copper particles which have been previously separated and have an average particle diameter of 1 to 200 micrometres. By means of this separation process particles with a high volume in relation to the surface area are obtained.

An additional improvement can be obtained by selecting an average particle diameter of less than or equal to 100 micrometres.

For typical use requirements it has proven appropriate to use average particle diameters of between 10 and 80 micrometres.

The average particle diameter is adapted to the required use conditions by at least comminuting any agglomerated portions of the at least partially oxidized copper.

It is possible to use a non-oscillating ball mill for carrying out the comminution process.

Another method of carrying out the comminution process is size reduction using a non-oscillating hammer mill.

In a preferred embodiment of the invention the oxidation process is carried out with at least partial sintering.

The invention also relates to a process for the production of an oxidic copper-based catalyst, in which molten metallic copper is atomised in a receiving medium having a temperature which is lower than the melting temperature of the copper, and the solidified copper particles are isolated and then oxidised.

The parameters specified for the catalyst obtained by atomization also apply to the process according to the invention.

The invention also relates to a process for the production of alkyl halosilanes by reacting silicon with alkyl halides at temperatures between 250° and 380° C., in which the catalyst according to the invention and optionally additional promoters are used.

Silicon of a purity of higher than 95% can be used as the silicon according to the invention. Silicon of a purity of higher than 98% is preferably used. The average particle diameter of the silicon used can be any required particle size, but is preferably between 50 and 500 $\mu$m.

The alkyl halides used according to the invention are all the customary $C_1$–$C_8$ alkyl halides, e.g. methylchloride, ethylchloride, propylchloride, etc. and preferably methyl chloride.

The use of the catalyst according to the invention does not of course rule out the employment of other known promoter substances, such as for example zinc or zinc compounds, phosphorus or phosphorus compounds, aluminium or aluminium compounds or tin or tin compounds which may be employed in the practice of this invention, either by themselves or in combination with one or more of the others.

Tin, phosphorus or zinc, either by themselves or in combination with one another, are preferably used, either in elemental form or in the form of their compounds.

The term compounds as used herein includes alloys.

The copper catalyst according to the invention is preferably used in a quantity of 0.05 to 10% by weight, and more preferably 0.5 to 7% by weight, based on silicon.

The process is usually carried out in the temperature and pressure range normally used for the Rochow synthesis, preferably between 280° and 390° C., and at a pressure of from 1 to 10 bars.

The process according to the invention is not limited to a particular processing technique in the direct synthesis. Thus the reaction can be carried out discontinuously or continuously and either in a fluidized, stirred or fixed bed.

The invention also relates to the use of the catalyst according to the invention for the production of alkyl halosilanes.

A further advantage of the catalyst according to the invention is that its catalytic activity is relatively independent of on the actual copper content.

The quantities of promoters mentioned above and hereinafter, such as for example the quantities of tin, are based on an analytical method of determination comprising ICP mass spectrometry using a Perkin Elmer Elan 500 device, and atomic emission spectrometry (ICP/AES) using a Perkin Elmer Optimal 3000 device.

The relative proportions of the individual copper phases were determined by X-ray diffraction using a Siemens D 5000 diffractometer.

The average particle diameter was determined by means of laser diffraction using a Malvern Master Sizer.

The following examples are intended to illustrate the present invention in more detail, although they must by no means be understood to be limitative.

PRACTICAL EXAMPLES

As far as the use of the catalysts according to the invention in the Rochow synthesis is concerned, the following experiments were carried out in a stirred bed reactor which is made of glass, has an internal diameter of 30 mm and is equipped with a spiral stirrer. Silicon having a purity of at least 98.8% and a particle size distribution of 71 to 160 $\mu$m was used.

The contact mass consisted of 40 g of silicon, 3.2 g of the copper catalyst described in more detail in the following tables and 0.05 g of ZnO and was homogenized before use.

Methyl chloride was passed through the contact mass from the bottom through a glas frit at a pressure of 2 bars. The rate of methyl chloride supplied to the reactor was kept constant and was approx. 1.8 l/h in all cases. Following the induction phase a stationary test phase was established at 300° C. Under these conditions the quantity of crude silane formed per unit of time was determined. The individual constituents were determined by gas chromatography.

Each of the indicated values is an average value between four individual measurements, and each test was rerun at least once.

EXAMPLE 1

To produce the copper catalyst, electrolytic copper was melted in an induction furnace, alloyed with tin and atomized with water at a water pressure of 300 bars. The resulting powder was dried, any particles with an average diameter smaller than 40 $\mu$m were separated off and oxidation was carried out at a temperature of 430° C. until the composition indicated in Table 1 was obtained.

For use in the stirred bed reactor, silicon of the above generally defined specifications containing 0.5% of Fe, 950 ppm of Al, 480 ppm of Ca and 230 ppm of Ti and the abovementioned copper catalyst were used.

Table 1 contains characteristic analytical data for the copper catalyst as well as the results of the Rochow synthesis carried out using the corresponding copper-containing catalysts.

In the comparative example, which is referred to in the last row of Table 1, silicon of the abovementioned specifications was used in combination with a copper catalyst according to U.S. Pat. No. 4 520 130 whose tin content was lower by comparison.

EXAMPLE 2

In order to produce the copper catalyst, electrolytic copper was melted in an induction furnace, alloyed with tin and atomized with water at a water pressure of 300 bars. The powder was dried, any contents with an average diameter smaller than 40 μm were separated off and oxidation was carried out at a temperature of 430° C. until the composition indicated in Table 1 was obtained.

For use in the Rochow reactor, silicon of the above generally defined specifications containing 0.45% of Fe, 0.21% of Al, 540 ppm of Ca and 230 ppm of Ti and the abovementioned copper catalyst were used.

Table 2 contains characteristic analytical data for the copper catalyst as well as the results of the Rochow synthesis carried out using the corresponding copper-containing catalysts.

In the comparative example which is referred to in the last row of Table 2, silicon of the abovementioned specifications was used in combination with a copper catalyst according to U.S. Pat. No. 4 520 130 whose tin content was lower by comparison.

in which $x+y+z=1$, a BET surface area of between 0.05 and less than 0.5 $m^2/g$ a lead content of less than 100 ppm and an average particle diameter of between 1 and 200 μm.

2. Copper-based catalysts according to claim 1, wherein $x=0$ to 0.3 and $x+y+z=1$ in said catalysts and they have a spongy surface at least before the oxidation of the metallic copper used as the starting substance.

3. Copper-based catalysts according to claim 1, wherein $x=0-0.3$, $y=0.2-0.9$ and $z=0.1-0.6$ and $x+y+z=1$.

4. Copper-based catalyst according to claim 1, wherein said catalysts are doped with at least one element selected from the group consisting of tin, zinc, aluminium, iron, antimony, arsenic, phosphorus, the alkali metals, the alkaline earth metals and combinations thereof, each of which is either in elemental form or in the form of one or more of their compound.

5. Copper-based catalysts according to claim 4, wherein said catalysts contain 1 to 3,000 ppm of tin and/or 1 to 3,000 ppm of zinc.

6. Copper-based catalysts obtainable by atomizing molten metallic copper in a receiving medium having a temperature

TABLE 1

| Test | Cu (%) | $Cu_2O$ (%) | CuO (%) | Sn (ppm) | Fe (ppm) | Pb (ppm) | BET ($m^2/g$) | Prod. rate (g/h) | McH (%) | Di (%) | Tri/Di |
|---|---|---|---|---|---|---|---|---|---|---|---|
| 1 | 14 | 71 | 15 | 120 | 240 | 50 | 0.8 | 7.6 | 1.9 | 91.6 | 0.044 |
| 2 | 13 | 72 | 15 | 160 | 330 | 53 | 1.0 | 7.5 | 1.8 | 91.8 | 0.043 |
| 3 | 13 | 74 | 13 | 190 | 510 | 83 | 1.3 | 7.8 | 1.4 | 91.8 | 0.045 |
| 4 | 17 | 66 | 17 | 250 | 70 | 7 | 0.8 | 7.2 | 1.2 | 92.3 | 0.041 |
| 5 | 9 | 65 | 26 | 270 | 70 | 4 | 0.8 | 7.3 | 1.7 | 91.7 | 0.041 |
| 6 | 1 | 72 | 27 | 62 | 20 | 11 | 1.4 | 7.7 | 1.9 | 91.7 | 0.044 |
| 7 | 1 | 71 | 28 | 160 | 230 | 10 | 1.5 | 8.4 | 1.4 | 92.6 | 0.041 |
| 8 | 18 | 52 | 30 | 230 | <20 | 9 | 0.2 | 6.6 | 1.5 | 92.2 | 0.043 |
| 9 | 18 | 55 | 27 | 74 | <20 | 9 | 1.0 | 6.2 | 1.6 | 90.7 | 0.053 |
| 10 | 17 | 50 | 33 | 73 | <20 | 9 | 0.4 | 6.6 | 1.7 | 91.0 | 0.048 |
| 11 | 24 | 28 | 48 | 170 | 110 | 8 | 0.3 | 7.0 | 1.4 | 90.8 | 0.052 |
| 12 | 23 | 31 | 46 | 160 | 130 | 9 | 1.0 | 7.9 | 1.3 | 90.6 | 0.056 |
| 13 | 26 | 32 | 42 | — | 130 | 7 | 0.5 | 7.0 | 1.4 | 89.9 | 0.059 |
| 14 | 21 | 35 | 44 | 97 | 160 | 67 | 0.3 | 6.0 | 1.6 | 91.1 | 0.051 |
| 15 | 22 | 39 | 39 | 490 | 160 | 66 | 1.0 | 6.7 | 1.5 | 91.2 | 0.049 |
| 16 | 23 | 40 | 37 | 82 | 170 | 66 | 0.4 | 6.4 | 1.4 | 91.8 | 0.045 |
| Comparison | 18 | 51 | 31 | 110 | 70 | 100 | 2.0 | 5.0 | 2.1 | 88.5 | 0.069 |

TABLE 2

| Test | Cu (%) | $Cu_2O$ (%) | CuO (%) | Sn (ppm) | Fe (ppm) | Pb (ppm) | BET ($m^2/g$) | Prod. rate (g/h) | McH (%) | Di (%) | Tri/Di |
|---|---|---|---|---|---|---|---|---|---|---|---|
| 17 | 11 | 24 | 65 | 510 | 180 | 74 | 0.2 | 6.7 | 2.1 | 91.0 | 0.049 |
| 18 | 44 | 18 | 38 | 690 | 870 | 85 | 0.4 | 7.8 | 1.2 | 91.6 | 0.048 |
| 19 | 26 | 61 | 18 | 520 | <20 | 6 | 0.7 | 8.0 | 1.3 | 92.2 | 0.043 |
| 20 | 22 | 58 | 20 | 570 | 40 | 7 | 0.7 | 8.2 | 1.6 | 91.6 | 0.045 |
| Comparison | 18 | 51 | 31 | 110 | 70 | 100 | 2.0 | 6.4 | 2.3 | 87.2 | 0.077 |

We claim:

1. Copper-based catalysts having the following composition:

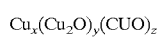

which is lower than the melting temperature of the copper, isolating the solidified copper particles and oxidizing same.

7. Copper-based catalysts according to claim 6, wherein the metallic copper is electrolytically produced copper.

8. Copper-based catalysts according to claim 6, wherein the receiving medium is water and/or oil.

9. Copper-based catalysts according to claim 6, wherein the receiving medium is selected from the group consisting of air, water vapour, oxygen, nitrogen, inert gas and combinations thereof.

10. Copper-based catalysts according to claim 6, wherein said catalysts are doped with at least one of the elements selected from the group consisting of tin, zinc, aluminium, iron, antimony, arsenic, phosphorus, the alkali metals, the alkaline earth metals and combinations thereof, either in elemental form or in the form of one or more of their compounds.

11. Copper-based catalysts according to claim 6, wherein said catalysts have a BET surface area of 0.05 to 1 $m^2/g$.

12. Copper-based catalyst according to claim 6, wherein the average particle diameter of said catalyst is 1 to 200 micrometres.

13. Process for the production of an oxidic copper-based catalyst, wherein molten metallic copper is atomized in a receiving medium having a temperature which is lower than the melting temperature of the copper and the solidified copper particles are isolated and oxidized.

14. Process according to claim 13, wherein the oxidation is carried out at temperatures between 300° C. and 900° C.

15. Process for the production of alkyl halosilanes by reacting silicon with alkyl halides in the presence of at least one copper-based catalyst and optionally at least one promoter, at temperatures between 250° and 380° C., wherein said process is carried out in the presence of a catalyst according to claim 1.

16. Process according to claim 15, wherein tin, zinc, aluminium, iron, antimony, arsenic, calcium, magnesium, phosphorus or a combination thereof, are used as promoters, either in elemental form or in the form of one or more of their compounds, in addition to the quantities contained in the copper-based catalyst.

* * * * *